United States Patent [19]

Hausser

[11] Patent Number: 5,342,309
[45] Date of Patent: Aug. 30, 1994

[54] SYRINGE HAVING SAFETY SHIELD

[75] Inventor: Roderick J. Hausser, Verona, N.J.

[73] Assignee: Becton, Dickinson and Company, Franklin Lakes, N.J.

[21] Appl. No.: 26,881

[22] Filed: Mar. 5, 1993

[51] Int. Cl.5 .............................................. A61M 5/00
[52] U.S. Cl. ..................................... 604/110; 604/198
[58] Field of Search ............... 604/110, 187, 192, 198, 604/263

[56] References Cited

U.S. PATENT DOCUMENTS

| | | | |
|---|---|---|---|
| 4,737,144 | 4/1988 | Choksi | 604/198 |
| 4,743,233 | 5/1988 | Schneider | 604/192 |
| 4,927,018 | 5/1990 | Yang et al. | 206/365 |
| 4,947,863 | 8/1990 | Haber et al. | 128/764 |
| 5,019,051 | 5/1991 | Hake | 604/198 |
| 5,024,660 | 6/1991 | McNaughton | 604/110 |
| 5,057,086 | 10/1991 | Dillard, III et al. | 604/198 X |
| 5,057,087 | 10/1991 | Harmon | 604/192 X |
| 5,057,087 | 10/1991 | Harmon | 604/198 |
| 5,059,185 | 10/1991 | Ryan | 604/198 |
| 5,067,945 | 11/1991 | Ryan et al. | 604/198 |
| 5,137,521 | 8/1992 | Wilkins | 604/263 X |
| 5,141,500 | 8/1992 | Hake | 604/198 |

Primary Examiner—John D. Yasko
Attorney, Agent, or Firm—John L. Voellmicke

[57] ABSTRACT

A hypodermic syringe has a syringe barrel with opposed proximal and distal ends and a fluid-receiving chamber therebetween. A tip at the distal end has a passage communicating with the fluid-receiving chamber. A needle hub is mounted to the tip and has a needle cannula mounted thereto. The needle hub includes a stop flange projecting radially outwardly therefrom and a locking wall projecting distally. A safety shield is mounted over the syringe barrel for telescoped movement from a proximal position where the needle cannula is exposed to a distal position where the needle cannula is protectively surrounded. Stop blocks on the safety shield engage the stop flange of the needle hub to prevent complete telescoped removal of the safety shield. Locking teeth on the safety shield engage with the locking wall on the needle hub to prevent proximal movement of the safety shield.

23 Claims, 6 Drawing Sheets

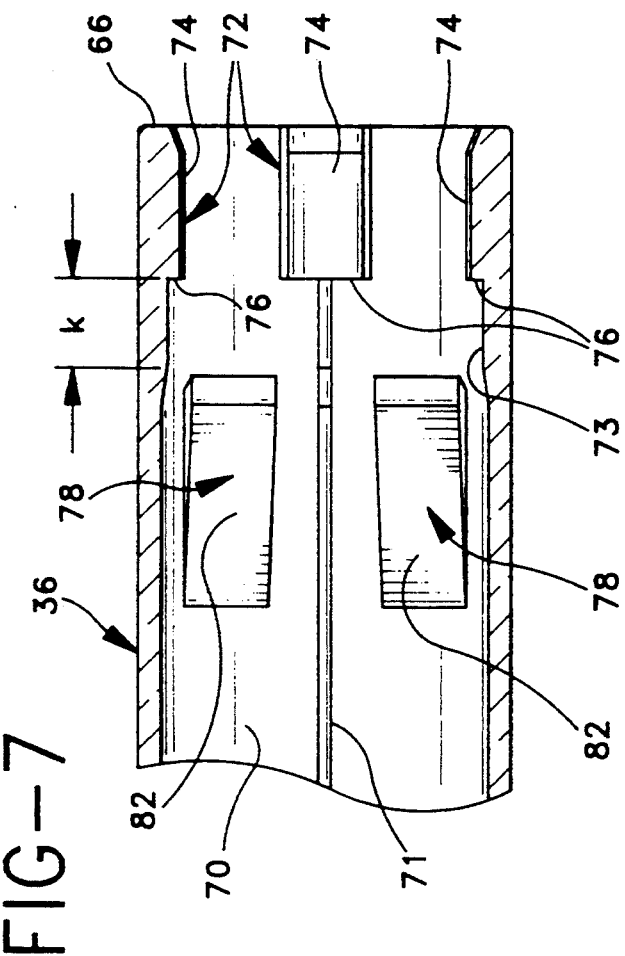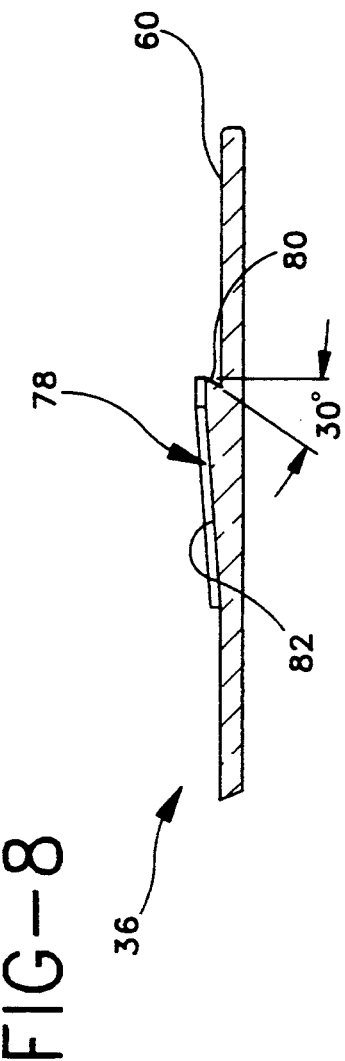

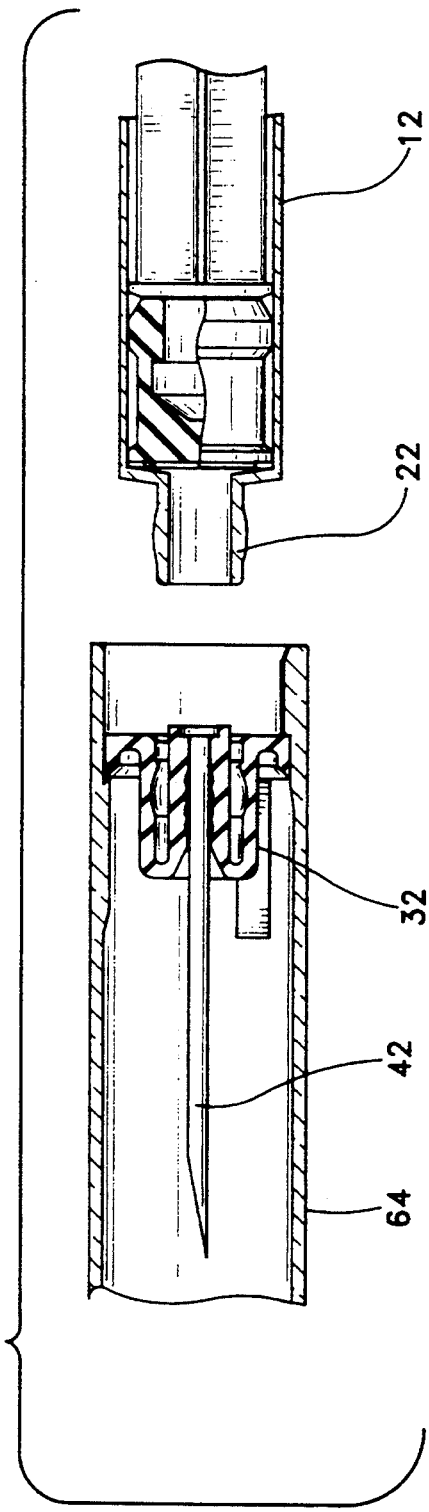
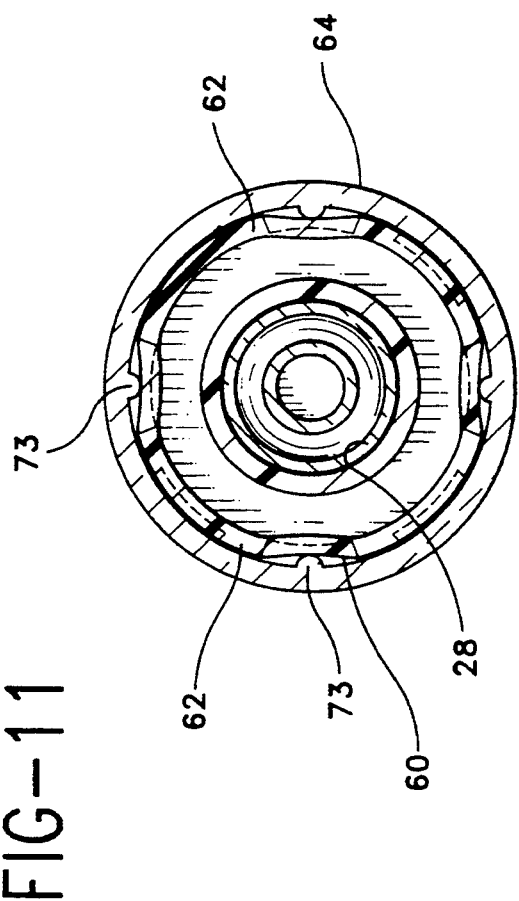
FIG-10
FIG-11

SYRINGE HAVING SAFETY SHIELD

FIELD OF THE INVENTION

The subject invention relates to a hypodermic syringe having a syringe barrel and sharp needle cannula. A rigid safety shield is telescoped over the syringe barrel, and can be moved from a proximal position where the needle cannula is exposed, to a distal position where the safety shield protectively surrounds the needle cannula for helping to prevent accidental needle sticks.

DESCRIPTION OF THE PRIOR ART

A hypodermic syringe includes a generally cylindrical syringe barrel with opposed proximal and distal ends. The proximal end is open and leads to a fluid-receiving chamber. The distal end defines a tip having a passage extending therethrough and communicating with the fluid-receiving chamber.

A needle cannula may be permanently engaged with a needle hub. The needle hub may then be threaded, snapped or otherwise engaged with the tip of the syringe barrel, such that the lumen of the needle cannula communicates with the passage through the tip.

Most hypodermic syringes having a cap-like shield mounted over the needle cannula by the manufacturer of the hypodermic syringe. This shield protects the needle from damage and contamination and protects the user from accidental needle sticks. The cap-like needle shield is removed and discarded when the hypodermic syringe is about to be used.

Accidental needle sticks that occur after the needle cannula has been used generally pose a greater health risk. To avoid such accidents, many prior art hypodermic syringes include a rigid cylindrical safety shield telescoped over the syringe barrel. The prior art safety shield can be slid from a proximal position where the needle cannula is exposed for use, to a distal position where the safety shield protectively surrounds the needle cannula.

Most prior art hypodermic syringes with cylindrical safety shields telescoped over the syringe barrel include structure for locking the safety shield in its distal position. The prior art locking means have included: bayonet connections requiring axial and rotational movement (U.S. Pat. No. 5,024,660; threaded interengagements (U.S. Pat. No. 4,743,233; and deflectable locking fingers (U.S. Pat. No. 4,737,144). Many of these prior art locking structures require additional components to be incorporated into the hypodermic syringe assembly, thereby increasing the complexity and total cost of the hypodermic syringes. Many prior art shieldable hypodermic syringes also are complicated to use in that they require twisting of the shield or other manipulations in addition to moving the shield to the extended, cannula-covering position.

Prior art hypodermic syringes also have been designed to make re-use of the syringe difficult or impossible. However, some of the prior art safety shields can be forceably telescoped beyond the distal end of the syringe barrel, thereby enabling re-use of the hypodermic syringe. Other prior art safety syringes do not prevent reuse and the safety shields can be urged proximally on the syringe barrel to re-expose the needle cannula.

SUMMARY OF THE INVENTION

The subject invention is directed to a hypodermic syringe having a syringe barrel with opposed proximal and distal ends. The proximal end of the syringe barrel is open and receives a plunger in sliding fluid-tight engagement. The distal end of the syringe barrel defines a tip having a passage extending therethrough and communicating with the chamber of the syringe barrel. The tip may include hub retention means for engaging a needle hub thereon. The retention means may be an annular ridge or an annular groove extending around an exterior surface of the tip.

A needle hub with a needle cannula affixed thereto is mounted to the distal end of the syringe barrel such that the lumen of the needle cannula communicates with the fluid-receiving chamber of the syringe barrel. The needle hub may include retention means to tightly engage the retention means on the tip of the syringe barrel.

The needle hub further includes a stop flange extending outwardly beyond the outer circumference of the syringe barrel. The stop flange includes a proximally facing stop surface which may be aligned generally orthogonally to the axis of the syringe barrel. The needle hub also includes a distally facing locking surface. The locking surface may include a generally concave distally facing chamfer.

A generally cylindrical safety shield is telescoped over the syringe barrel and can be slid from a proximal position where the needle cannula is exposed, to a distal position where the safety shield protectively surrounds the needle cannula. The inner circumferential surface of the safety shield is characterized by inwardly projecting stop means for preventing complete telescoped removal of the safety shield from the syringe barrel. The stop means of the safety shield is dimensioned and disposed to engage the stop face on the stop flange of the needle hub. The stop means of the safety shield may be operative to urge the needle hub inwardly into tighter engagement with the tip of the syringe barrel.

The stop means of the safety shield may also be dimensioned to releasably retain the safety shield in its proximal position on the syringe barrel. For example, the stop means may frictionally engage an outer circumferential surface region at the proximal end of the syringe barrel. Opposed axial forces can be exerted on the safety shield and the syringe barrel to overcome these frictional engagement forces and enable distal movement of the safety shield relative to the syringe barrel and the needle cannula.

The safety shield further is provided with inwardly extending locking means for lockingly engaging the locking surface of the needle hub to prevent proximal movement of the safety shield after the needle cannula has been protectively surrounded. The locking means may comprise at least one rigid locking tooth that is ramped to deflect the needle hub inwardly as the safety shield is moved distally over the needle hub. However, the locking tooth will pass distally beyond the flange of the needle hub after sufficient movement of the safety shield along the syringe barrel. At that point, the needle hub will resiliently return toward an undeflected condition, with the locking surface and the stop surface of the needle hub locked between the locking tooth and the stop means of the safety shield.

The locking tooth of the safety shield may include a proximally facing locking surface that is undercut to engage the chamfered concave locking surface on the flange of the needle hub. Thus, the undercut locking surface on the safety shield will urge the needle hub radially outwardly in response to proximal forces exerted on the safety shield. As a result, the needle hub will bite into the safety shield to increase locking resistance and prevent re-exposure of the needle cannula.

Conceivably, excessive distally directed forces on the safety shield could overcome the retention forces between the needle hub and the tip of the syringe barrel. However, the needle hub will remain trapped between the stop means and the locking means of the safety shield, with the needle cannula protectively surrounded by the safety shield. As a result, even if the safety shield is forceably removed, the hypodermic syringe will be rendered safe and substantially unusable and the used needle cannula will remain protectively surrounded by the safety shield.

BRIEF DESCRIPTION OF THE DRAWINGS

FIG. 6 is an end elevational view of a safety shield in accordance with the subject invention.

FIG. 7 is a cross-sectional view taken along line 7—7 in FIG. 6.

FIG. 8 is a cross-sectional view taken along line 8—8 in FIG. 6.

FIG. 10 is an exploded cross-sectional view similar to FIG. 9, but showing the safety shield forceably separated from the syringe barrel.

FIG. 11 is a cross-sectional view of the syringe of FIG. 9 taken along line 11—11.

DETAILED DESCRIPTION OF THE PREFERRED EMBODIMENT

Figure 1:
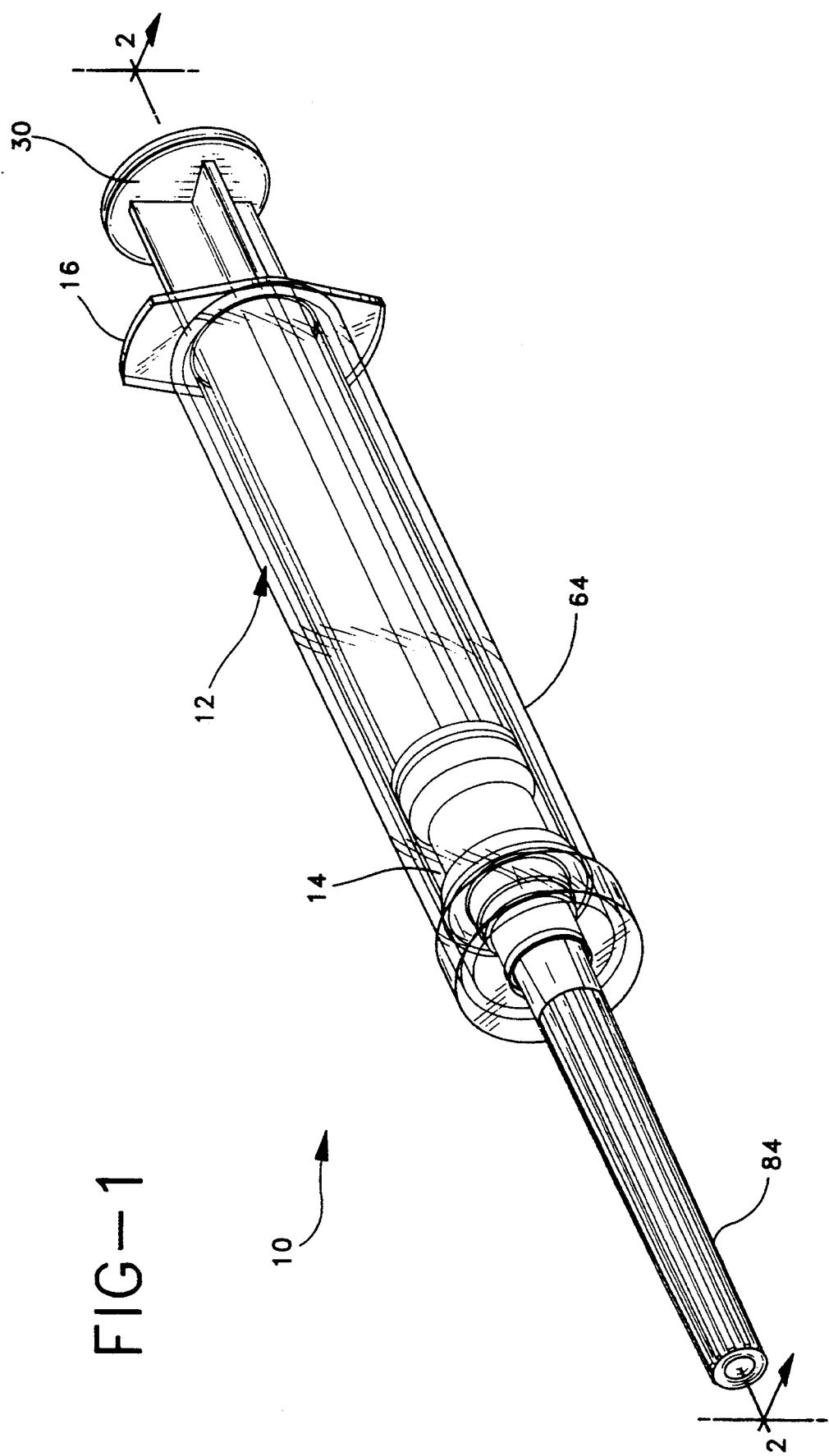
FIG. 1 is a perspective view of a hypodermic syringe incorporating a safety shield in accordance with the subject invention.
Figure 2:
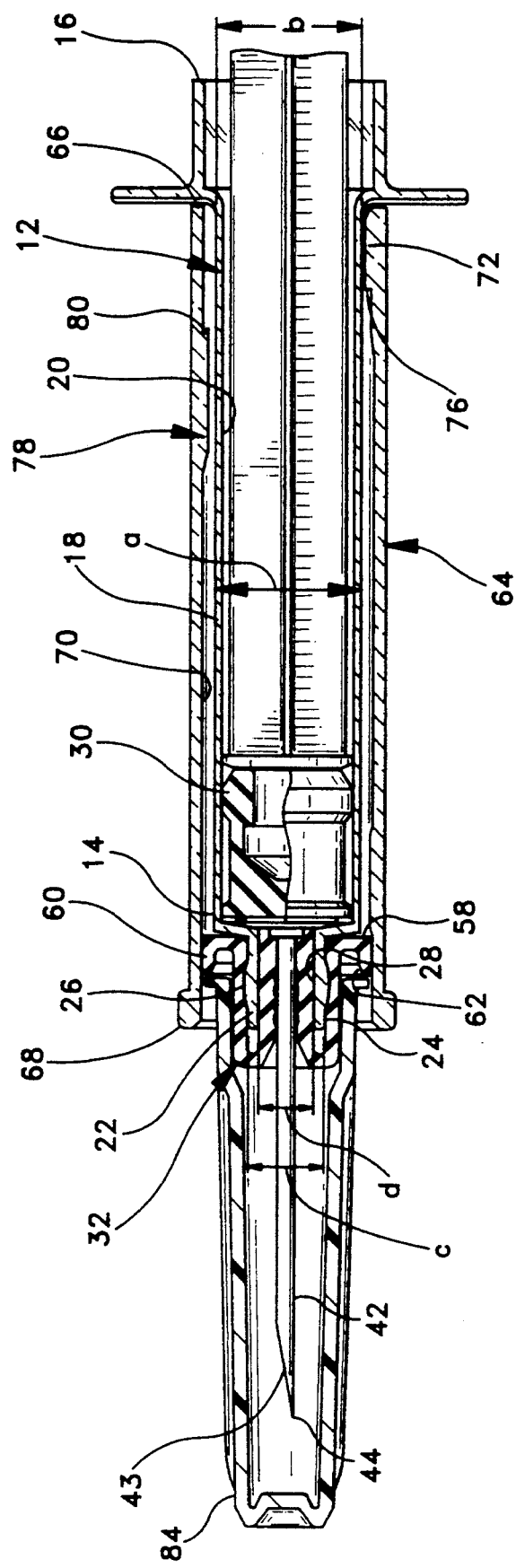
FIG. 2 is a cross-sectional view taken along line 2—2 in FIG. 1.

A syringe assembly in accordance with the subject invention is identified generally by the numeral 10 in FIGS. 1 and 2. Hypodermic syringe 10 includes a generally cylindrical syringe barrel 12 having a distal end 14, an open proximal end 16 and a generally cylindrical wall 18 extending therebetween.

Cylindrical wall 18 of syringe barrel 12 defines a fluid-receiving chamber 20 leading into open proximal end 16. Cylindrical wall 18 defines an outside diameter "a"" along most of the length of cylindrical wall 18. However, portions of cylindrical wall 18 near proximal end 16 of syringe barrel 12 define a major outside diameter "b".

Distal end 14 of syringe barrel 12 defines a tip 22 having a generally cylindrical outer surface 24 defining an outside diameter "c" along a major portion of the length of tip 22. However, an outwardly extending retention rib 26 is defined in outer circumferential surface 24 intermediate the axial length of tip 22. Tip 22 is further characterized by a passage 28 of inside diameter "d" extending entirely therethrough and into communication with chamber 20 of syringe barrel 12.

A plunger 30 is slidably disposed in chamber 20 in fluid-tight engagement with cylindrical wall 18. Thus, movement of plunger 30 in a distal direction urges fluid in chamber 20 through passage 28 and from syringe barrel 12. Conversely, movement of plunger 30 in a proximal direction creates a low pressure in chamber 20 that draws fluid through passage 28 and into chamber 20.

A needle hub 32 is mounted to tip 22 at distal end 14 of syringe barrel 12. Needle hub 32 is unitarily molded from a thermoplastic material, such as polypropylene. Needle hub 32 is a generally annular structure, as shown most clearly in FIGS. 3 and 4, with opposed proximal and distal ends 34 and 36 respectively. An inner mounting sleeve 38 extends from proximal end 34 toward distal end 36. Inner mounting sleeve 38 includes a needle passage 40 extending axial therethrough for receiving a proximal end of needle cannula 42, as shown in FIG. 2. More particularly, an epoxy or other such permanent sealing and retention means is continuously engaged between needle cannula 42 and inner mounting sleeve 38. Needle cannula 42 further includes a sharp point or cutting edge 44 projecting axial therefrom at distal end 43 of the cannula.

Inner mounting sleeve 38 further includes an outer circumferential surface 46 defining a diameter "e", which is preferably approximately equal to or slightly greater than inside diameter "d" of passage 28 extending through syringe tip 22. Thus, inner mounting sleeve 38 can be slidably inserted into passage 28 and frictionally retained therein.

Needle hub 32 further includes an outer mounting sleeve 48 which projects proximally from the distal end 36 of needle hub 32. Outer mounting sleeve 48 includes an inner circumferential surface 50 defining an inside diameter "f" approximately equal to or slightly less than outside diameter "c" defined by outer circumferential surface 24 of syringe tip 22. However, inner circumferential surface 50 of outer mounting sleeve 48 is characterized by an outwardly extending retention groove 52 dimensioned and disposed to be engaged by retention rib 26 in outer circumferential surface 24 of syringe tip 22. Thus, syringe tip 22 can be frictionally retained in the generally annular space 54 between inner mounting sleeve 38 and outer mounting sleeve 48 of needle hub 32. In addition to the frictional retention, the outwardly extending retention groove 52 of needle hub 32 is mechanically engaged by retention rib 26 of syringe tip 22.

Needle hub 32 is further characterized by a stop flange 56 projecting outwardly from outer mounting sleeve 48 at proximal end 34 of needle hub 32. Stop flange 56 includes a proximally facing stop surface 58 aligned generally radially at proximal end 34 of needle hub 32 and defining an outside diameter "g" greater than outside diameters "a" or "b" along syringe barrel 12.

Figure 4:
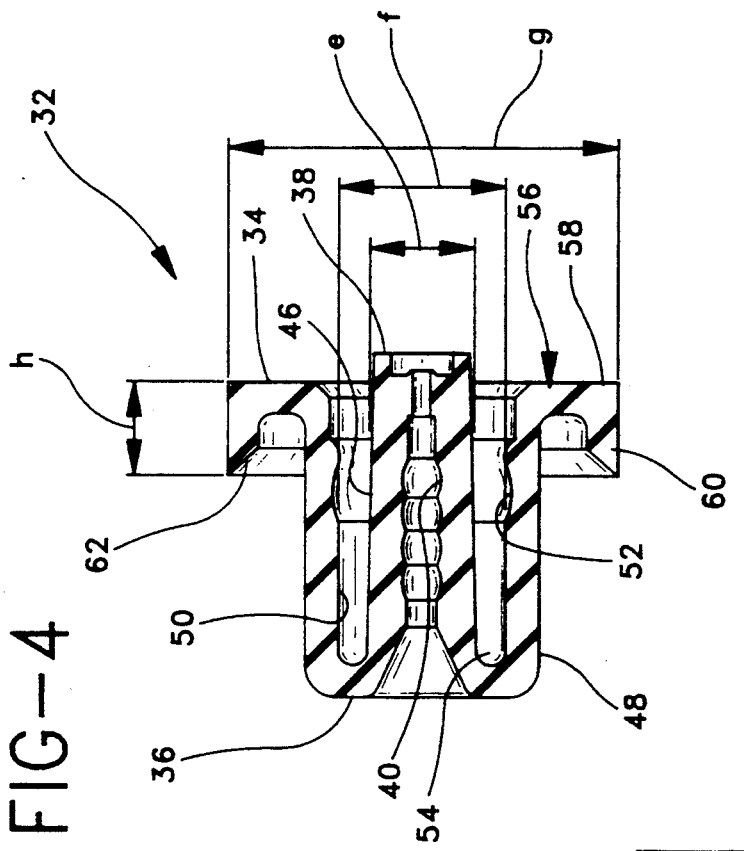
FIG. 4 is a cross-sectional view taken along line 4—4 in FIG. 3.
Figure 5:
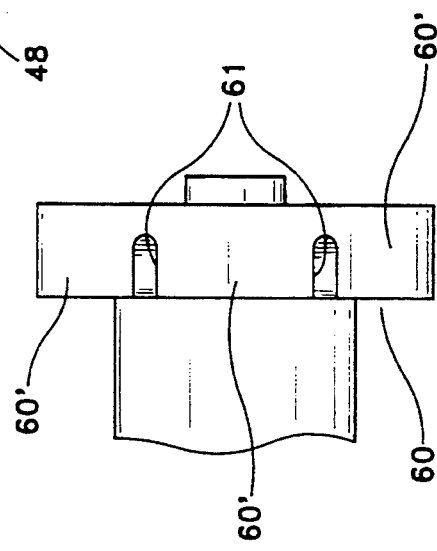
FIG. 5 is a partial side elevational view of an alternate needle hub in accordance with the subject invention.
Figure 3:
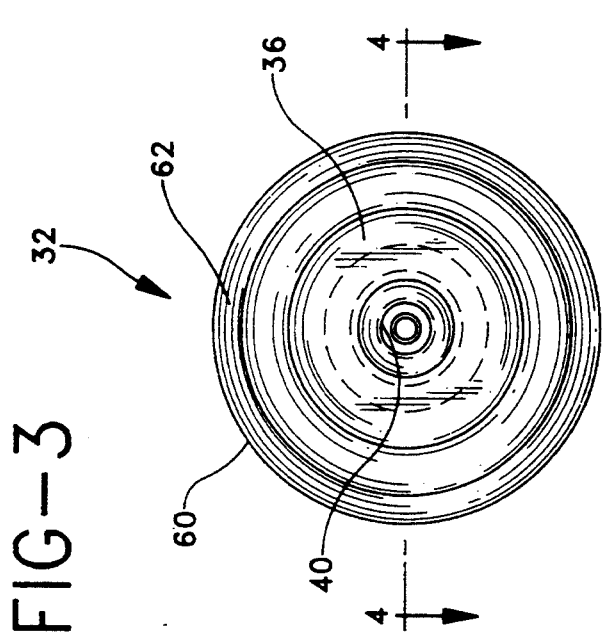
FIG. 3 is an end elevational view of the needle hub of the subject invention.

A preferably annular-shaped locking wall 60 projects distally from stop flange 56 and is spaced radially outwardly from outer mounting sleeve 48. Locking wall 60 defines a total axial length "h" as shown in FIG. 4. The distal end of locking wall 60 defines an inwardly chamfered locking surface 62 which is aligned to a radius of needle hub 32 preferably at an angle of approximately 30°. In this embodiment the locking surface is preferably slightly concave in shape. As shown in FIGS. 3 and 4, locking wall 60 is a substantially continuous annular structure. However, with reference to FIG. 5, a plurality of axial extending slits 61 may be defined in locking wall 60. More particularly, slits 61 define locking wall segments 60' that can be deflected more easily outwardly in view of the substantial absence of hoop stress.

Hypodermic syringe 10 further includes a safety shield 64 telescoped over syringe barrel 12. Safety shield 64 includes opposed proximal and distal ends 66 and 68 and a generally cylindrical inner surface 70.

As shown in FIGS. 6–8, a plurality of circumferentially spaced stop blocks 72 project inwardly from cylindrical inner surface 70 at locations adjacent proximal end 66 of safety shield 64. Stop blocks 72 include inwardly facing surface 74 which define an inside diameter "i" which is approximately equal to or slightly less than the major diameter "b" at proximal end 16 of syringe barrel 12. However, inside diameter "i" defined by inwardly facing surfaces 74 of stop locks 72 is significantly less than the major diameter "g" defined by stop surface 58 of needle hub 32. Stop blocks 72 further include distally facing stop surfaces 76 which are aligned substantially radially. As will be explained further herein, the stop surfaces 76 of stop blocks 72 will engage against stop surface 58 of needle hub 32 to prevent complete telescoped removal of safety shield 64 from syringe barrel 12.

Inner circumferential surface 70 of safety shield 64 is further characterized by inwardly directing locking teeth 78. Locking teeth 78 are characterized by proximally facing locking surfaces 80 and distally facing ramp surfaces 82. Locking surfaces 80 are preferably aligned to a radius of safety shield 64 at an angle approximately equal to the angle of locking surface 62 on needle hub 32. Opposed locking surfaces 80 on safety shield 64 define a minor inside diameter "j" which is less than the outside diameter "g" of locking wall 60 on needle hub 32. As shown most clearly in FIG. 7, locking teeth 78 are spaced distally from stop blocks 72 by distance "k" which is slightly greater than axial length "h" of locking wall 60. Thus, as will be explained further herein, locking wall 60 can be trapped axially intermediate stop blocks 72 and locking teeth 78.

Hypodermic syringe 10 is assembled by initially urging safety shield 64 over syringe barrel 12 in a distal to proximal direction. Lock blocks 72 will frictionally engage over the major diameter portion of syringe barrel 12 adjacent proximal end 16 thereof. Needle cannula 42, in this embodiment, is permanently affixed in needle hub 32 by epoxy or other known means. A needle shield 84 may be mounted over needle cannula 42 and frictionally retained in the space between outer mounting sleeve 48 and locking wall 60 to protect against accidental needle sticks prior to use of hypodermic syringe 10. The combined needle hub 32, needle cannula 42 and needle shield 84 are then advanced in a distal to proximal direction over distal end 14 of syringe barrel 12. More particularly, syringe tip 22 is urged into annular space 54 between inner and outer mounting sleeves 38 and 48 respectively. After sufficient axial advancement, retention groove 52 of needle hub 32 will be engaged by retention groove 26 of syringe tip 22. The engagement of retention groove 52 with retention rib 26 and the frictional engagement of inner and outer mounting sleeves 38 and 48 with syringe tip 22 securely retains needle hub 32 on syringe barrel 12 to complete the assembly.

Hypodermic syringe 10 may be prepared for use by removing needle shield 84 from needle hub 32 to expose needle cannula 42 for use. Immediately after use safety shield 64 of hypodermic syringe 10 can be slid distally relative to syringe barrel 12. Sufficient distal movement of safety shield 64 will cause ramp surfaces 82 of locking teeth 78 to engage the exterior of annular locking wall 60 on needle hub 32. Further distal movement will cause locking wall 60 to deflect inwardly sufficiently to enable continued distal movement of safety shield 64. After sufficient distal movement, however, locking teeth 78 will pass distally beyond locking wall 60, thereby enabling locking wall 60 to resiliently return toward an undeflected condition. In this disposition locking wall 60 will be trapped intermediate stop blocks 72 and locking teeth 78 of safety shield 64. Attempts to move safety shield 64 further in a distal direction are resisted by engagement of stop blocks 72 with stop surfaces 58 of stop flanges 56. Inward deflection of locking wall 60 is resisted by the locking teeth 78 substantially adjacent the distally facing locking surface 62 of locking wall 60. Additionally, these distally directed forces on safety shield 64 will urge retention groove 52 of needle hub 32 into tighter engagement with retention rib 26 of tip 22 on syringe barrel 12.

Proximally directed forces on safety shield 64 that could re-expose needle cannula 42 are resisted by engagement between locking surfaces 80 of locking teeth 78 on safety shield 64 with locking surface 62 on locking wall 60 of needle hub 32. The angular alignments of locking surface 62 on locking wall 60 and locking surfaces 80 on locking teeth 78 will cause locking flange 56 to deflect outwardly and into tighter locked engagement with safety shield 64 when increased distally directed force is applied to safety shield 64.

Conceivably, extreme axial forces could be exerted on safety shield 64 in an effort to remove safety shield 64 from hypodermic syringe 10 and to re-expose needle cannula 42. However, such extreme axial forces would cause needle hub 32 to be separated from syringe barrel 12 before causing a separation of safety shield 64 from needle hub 32. Thus, as shown most clearly in FIG. 10, excessive distally directed forces on safety shield 64 would cause simultaneous separation of safety shield 64, needle hub 32 and needle cannula 42 from syringe barrel 12, thereby leaving a substantially useless and harmless syringe barrel 12, while keeping the previously used needle cannula 42 safety protected and trapped within safety shield 64.

Accordingly, it is within the purview of this invention to design the barrel tip of the needle hub to allow removal of the hub, when it is trapped in the safety shield and to use the safety shield as a needle disposal device. Also, the hub and the barrel tip could be designed to stay connected permanently and to resist manually applied force applied to the safety shield in a distal direction.

Figure 9:
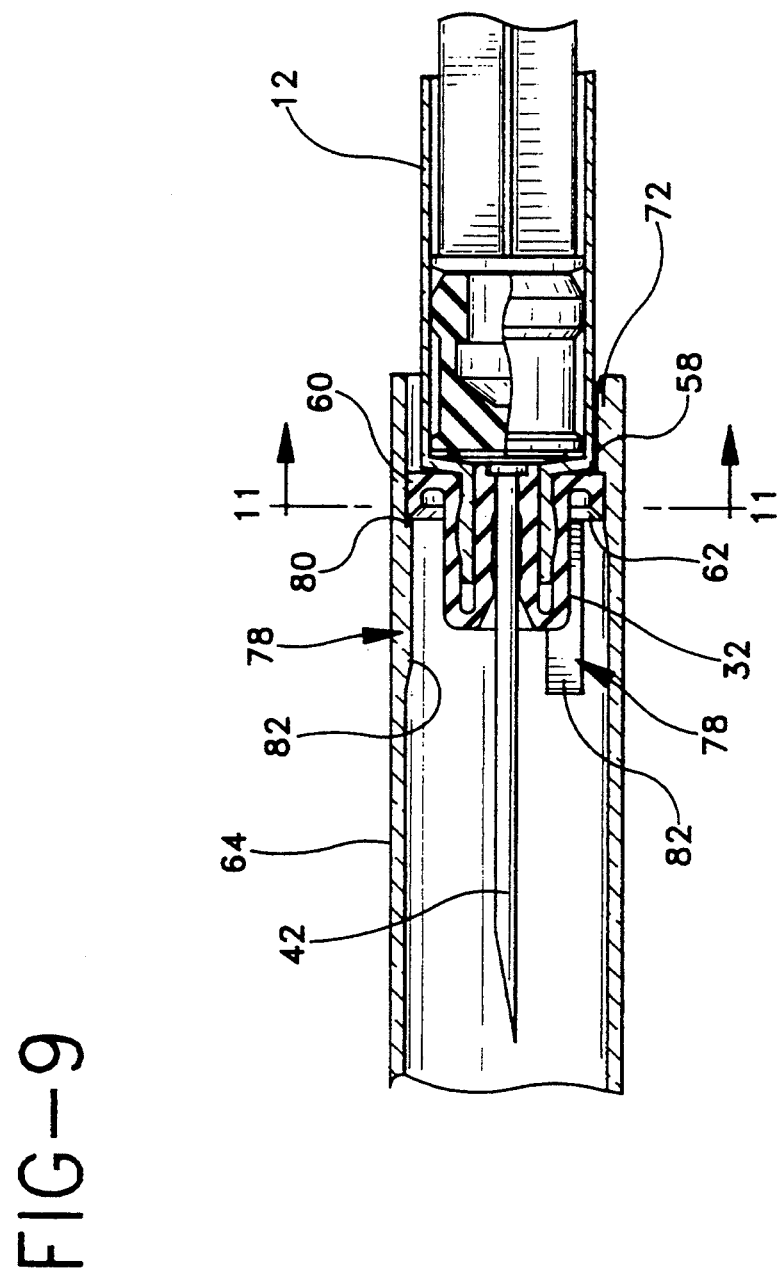
FIG. 9 is a cross-sectional view similar to FIG. 2 but showing the safety shield in its distal locked position surrounding the needle cannula.

Longitudinal ribs 71, as best illustrated in FIG. 7, are enlarged in the area between locking teeth 78 and stop block 72, as indicated by numeral 73. When safety shield 64 is in the extended locked position, as illustrated in FIGS. 9 and 11, rib portion 73 further enhances the locking relationship between locking surface 62 of locking wall 60 and locking surfaces 80 of locking teeth 78 by forcing the locking wall into a non-circular shape having its largest diameter where locking surface 62 engages locking surface 80 of the locking teeth.

What is claimed is:

1. A syringe assembly comprising:
  a hypodermic syringe having a syringe barrel with opposed proximal and distal ends, and a fluid-receiving chamber therein, said distal end defining a tip having a passage extending therethrough and communicating with said chamber;

a needle hub securely mounted to said tip of said syringe barrel and having a needle cannula affixed thereto for communicating with said fluid-receiving chamber, said needle hub comprising a proximally facing stop surface projecting radially outwardly beyond portions of said syringe barrel adjacent said tip, and at least one deflectable locking wall projecting distally and outwardly from said hub; and said locking wall including a substantially annular distally facing locking surface; and a safety shield mounted over said syringe barrel for telescoping movement from a proximal position where said needle cannula is exposed to a distal position where said safety shield protectively surrounds said needle cannula, said safety shield including at least one stop block projecting inwardly therefrom, said stop block being engageable with said stop surface of said needle hub for preventing removal of said safety shield from said syringe barrel, said safety shield further comprising at least one locking tooth dimensioned and disposed to generate inward deflection of said locking wall of said hub during said telescoping movement of said safety shield from said proximal position toward said distal position, said locking tooth being spaced distally from said stop block a sufficient distance to enable engagement of said stop surface and said locking surface of said hub between said stop block and said locking tooth of said safety shield, and said locking tooth being configured to engage said deflectable locking wall to prevent proximal movement of said safety shield from its distal position.

2. A syringe assembly as in claim 1, wherein said deflectable locking wall is a continuous frusto-conically shaped wall.

3. A safety assembly as in claim 1, wherein said needle hub includes a generally radially aligned stop flange on which said stop surface is defined and said locking wall projecting distally from the stop flange, said locking surface being distally disposed on said locking wall.

4. A safety assembly as in claim 3, wherein said locking surface of said needle hub is chamfered to generate outward deflection of said locking wall in response to proximally directed forces applied through said locking tooth.

5. A safety assembly as in claim 3, wherein said locking wall defines a continuous annular wall.

6. A safety assembly as in claim 3, wherein said at least one locking wall comprises a plurality of independently resiliently deflectable locking walls projecting distally from said stop flange.

7. A safety assembly as in claim 1, wherein said needle hub includes an inner mounting sleeve dimensioned for engagement in said passage of said tip of said syringe barrel and an outer mounting sleeve dimensioned for secure engagement around said tip.

8. A safety assembly as in claim 1, wherein said tip of said syringe barrel and said needle hub include interengageable retention means for securely retaining said needle hub on said tip.

9. The syringe assembly of claim 8 wherein said interengageable retention means is configured to allow the hub to be forceably removed from said tip through distal axial movement of said safety shield with respect to said barrel.

10. A safety assembly as in claim 1, wherein said safety shield comprises a plurality of said stop blocks disposed in circumferentially spaced relationship about said safety shield, said stop blocks being dimensioned to releasably engage said syringe barrel adjacent said proximal end thereof.

11. A safety assembly as in claim 1, wherein said safety shield comprises a plurality of locking teeth, each said locking tooth having a proximally facing locking surface undercut to generate outward deflection of said locking wall of said needle hub in response to proximally directed forces on said safety shield relative to said syringe barrel, whereby outward deflection of said locking wall urges said locking wall into said safety shield for secure locking retention of said safety shield relative to said needle hub.

12. A syringe assembly as in claim 2 wherein said at least one locking tooth comprises a plurality of circumferentially spaced locking teeth.

13. A syringe assembly as in claim 12 wherein said locking collar includes a plurality of inwardly projecting, longitudinally oriented, circumferentially spaced ribs at its proximal end, said ribs being positioned between said plurality of circumferentially spaced locking teeth, said ribs being sized to define a diameter which is less than the outside diameter defined by said locking wall so that when said safety shield is in said locked distal position said ribs force said locking wall into a non-circular shape having its largest diameter where said locking wall engages said locking teeth.

14. The syringe assembly as in claim 1, wherein said cannula includes a distal end having a sharp cutting edge.

15. A safety assembly as in claim 1, wherein said needle hub is molded from a resiliently deflectable thermoplastic material.

16. A syringe assembly comprising:

a hypodermic syringe having a syringe barrel with opposed proximal and distal ends, and a fluid-receiving chamber therein, said distal end defining a tip having a passage extending therethrough and communicating with said chamber;

a needle hub securely mounted to said tip of said syringe barrel and having a needle canal affixed thereto for communicating with said fluid-receiving chamber, said needle hub comprising a proximally facing stop surface projecting radially outwardly beyond portions of said syring barrel adjacent said tip, and at least one deflectable locking wall projecting distally and outwardly from said hole, and said locking wall including a distally facing locking surface; and a safety shield mounted over said syringe barrel for telescoping movement from a proximal position where said needle cannula is exposed to a distal position where said safety shield protectively surrounds said needle cannula, said safety shield including at least one stop block projecting inwardly therefrom, said stop block being engageable with said stop surface of said needle hub for preventing removal of said safety shield from said syringe barrel, said safety shield further comprising at least one locking tooth dimensioned and disposed to generate inward deflection of said locking wall of said hub during said telescoping movement of said safety shield from said proximal position toward said distal position, said locking tooth being spaced distally from said stop block a sufficient distance to enable engagement of said stop surface and said locking surface of said hub between said stop block and said locking tooth of said safety shield while allowing relative rotation between said safety shield and said needle hub when said stop surface and said locking surface of said hub are positioned between said stop block and said locking tooth of said safety shield, and said locking tooth being configured to engage said deflectable locking wall to prevent proximal movement of said safety shield from its distal position.

17. A syringe assembly as in claim 16, wherein said deflectable locking wall is a continuous frusto-conically shaped wall.

18. A safety assembly as in claim 16, wherein said needle hub includes a generally radially aligned stop flange on which said stop surface is defined and said locking wall projecting distally from the stop flange, said locking surface being distally disposed on said locking wall.

19. A safety assembly as in claim 18, wherein said locking surface of said needle hub is chamfered to generate outward deflection of said locking wall in response to proximally directed forces applied through said locking tooth.

20. A safety assembly as in claim 18, wherein said locking wall defines a continuous annular wall.

21. A safety assembly as in claim 18, wherein said at least one locking wall comprises a plurality of independently resiliently deflectable locking walls projecting distally from said stop flange.

22. A safety assembly as in claim 16, wherein said safety shield comprises a plurality of said stop blocks disposed in circumferentially spaced relationship about said safety shield, said stop blocks being dimensioned to releasably engage said syringe barrel adjacent said proximal end thereof.

23. A safety assembly as in claim 16, wherein said safety shield comprises a plurality of locking teeth, each said locking tooth having a proximally facing locking surface undercut to generate outward deflection of said locking wall of said needle hub in response to proximally directed forces on said safety shield relative to said syringe barrel, whereby outward deflection of said locking wall urges said locking wall into safety shield for secure locking retention of said safety shield relative to said needle hub.

* * * * *